United States Patent
Sawhney et al.

(10) Patent No.: US 6,379,373 B1
(45) Date of Patent: *Apr. 30, 2002

(54) METHODS AND APPARATUS FOR INTRALUMINAL DEPOSITION OF HYDROGELS

(75) Inventors: Amarpreet S. Sawhney, Lexington; John Spiridigliozzi, Boston, both of MA (US)

(73) Assignee: Confluent Surgical, Inc., Waltham, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/390,046

(22) Filed: Sep. 3, 1999

Related U.S. Application Data

(63) Continuation-in-part of application No. 09/133,950, filed on Aug. 14, 1998, now Pat. No. 6,152,943.

(51) Int. Cl.$^7$ ............................................. A61M 29/00
(52) U.S. Cl. ........................................ 606/193
(58) Field of Search ............................... 606/193, 194, 606/191, 192; 604/102.02, 102.03, 96.01

(56) References Cited

U.S. PATENT DOCUMENTS

| | | | |
|---|---|---|---|
| 3,640,741 A | 2/1972 | Etes | ............................ 106/170 |
| 3,865,108 A | 2/1975 | Hartop | ........................ 128/260 |

(List continued on next page.)

FOREIGN PATENT DOCUMENTS

| WO | WO 95/08289 | 3/1995 | ............. A61F/2/06 |
|---|---|---|---|

OTHER PUBLICATIONS

Abusafieh A. et al., "Development of Self–Anchoring Bone Implants. I. Processing and Material Characterization," *J. Biomat. Mater. Res.*, (Appl. Biomater.), 38:314–327 (1997).

Bhatia, S. et al., "The Effect of Siteof Implantation and Animal Age on Properties of Polydioxanone Pins," *J. Biomater. Sci., Polymer. Edn.*, Bamford, C.H. et al., eds., 6(5): 435–446 (1994).

Brundin, J., "Hydrogel Tubal Blocking Device: P–Block," *Female Transcervical Sterilization*, Zatuchni, G.I. et al., eds., Harper & Row, Philadelphia, Pennsylvania, 240–244(1982).

Chisholm, R.A. et al., "Fibrin Sealant as a Plug for the Post Liver Biopsy Needle Track," *Clinical Radiology*, 40(6):627–628 (1989).

Greenberg, A.R. et al., "Stimulation of Bone Formation by a Swelling Endosseous Implant," *J. Biomed. Maters. Research*, 12:929–933 (1978).

*Handbook of Common Polymers*, compiled by Roff, W.J. et al., CRC Press, Cleveland, Ohio.

(List continued on next page.)

Primary Examiner—Michael Buiz
Assistant Examiner—Kevin Truong
(74) Attorney, Agent, or Firm—Patterson, Thuenten, Skaar & Christensen, P.A.

(57) ABSTRACT

Methods and apparatus of forming hydrogel systems in situ are provided using a delivery system configured to deliver two or more fluent prepolymer solutions without premature crosslinking. The delivery system comprises separate first and second lumens coupling first and second inlet ports and first and second outlet ports, respectively, and may include a balloon, flexible distal region, mixing chamber or steerable distal end. Multi-component hydrogel systems suitable for use with the inventive methods and apparatus are also described.

13 Claims, 2 Drawing Sheets

U.S. PATENT DOCUMENTS

| | | | |
|---|---|---|---|
| 3,991,766 A | 11/1976 | Schmitt et al. | 128/335.5 |
| 3,992,562 A | 11/1976 | Denzinger et al. | 526/208 |
| 4,002,173 A | 1/1977 | Manning et al. | 128/296 |
| 4,014,335 A | 3/1977 | Arnold | 128/260 |
| 4,207,893 A | 6/1980 | Michaels | 128/260 |
| 4,369,229 A | 1/1983 | Shah | 428/421 |
| 4,655,771 A | 4/1987 | Wallsten | 623/1 |
| 4,741,872 A | 5/1988 | DeLuca et al. | 264/4.7 |
| 4,762,129 A | 8/1988 | Bonzel | 128/344 |
| 4,826,945 A | 5/1989 | Cohn et al. | 528/76 |
| 4,938,763 A | 7/1990 | Dunn et al. | 604/891.1 |
| 5,067,497 A | 11/1991 | Greear et al. | 128/207 |
| 5,090,995 A | 2/1992 | Kubota et al. | 71/114 |
| 5,100,992 A | 3/1992 | Cohn et al. | 528/26 |
| 5,160,745 A | 11/1992 | DeLuca et al. | 424/487 |
| 5,171,148 A | 12/1992 | Wasserman et al. | 433/215 |
| 5,198,220 A | 3/1993 | Damani | 424/426 |
| 5,324,775 A | 6/1994 | Rhee et al. | 525/54.2 |
| 5,328,471 A | 7/1994 | Slepian | 604/101 |
| 5,410,016 A | 4/1995 | Hubbell et al. | 528/354 |
| 5,476,434 A * | 12/1995 | Kalb et al. | 606/193 |
| 5,522,898 A | 6/1996 | Bao | 623/17 |
| 5,645,583 A | 7/1997 | Villain et al. | 623/5 |
| 5,785,679 A | 7/1998 | Abolfathi et al. | 604/51 |
| 5,830,196 A | 11/1998 | Hicks | 604/280 |
| 5,895,405 A | 4/1999 | Inderbitzen | 606/194 |
| 5,904,665 A * | 5/1999 | Muharib | 606/193 |

OTHER PUBLICATIONS

Jarrett P.K. et al., "Bioabsorbable Hydrogel Tissue Barrier: In Situ Gelation Kinetics," *Soc. for Biomater.*, Transactions of 21st Annual Meeting:182 (1995).

*Medicinal Chemistry*, 3rd Ed., Parts 1 and 2, Burger, A., ed., Wiley–Interscience.

Nagaoka, S. et al., "Interaction Between Blood Components and Hydrogels with Poly(oxyethylene) Chains," *Polymers As Biomaterials*, Shalaby, S.W. et al., eds., Plenum Press, New York, 361–374 (1984).

Okano, T. et al., "Effect of Hydrophilic and Hydrophobic Microdomains on Mode of Interaction Between Block Polymer and Blood Platelets," *J. Biomed. Mats.. Research*, 15:393–402 (1981).

Onishi, Y. et al., "Study of Dextran–Methyl Methacrylate Graft Copolymer," *Contemporary Topics in Polymer Science*, Bailey, W.J. et al., eds., Plenum Press, New York, 4:149–162 (1984).

Park, K., "Enzyme–Digestible Swelling Hydrogels as Platforms for Long–Term Oral Drug Delivery: Synthesis and Characterization," *Biomaterials*, 9:435–441) (1988).

Park, K. et al., *Biodegradable Hydrogels for Drug Delivery*, Technomic Publshing Co., Inc., Lancaster, Pennsylvania (1993).

*Remington's Pharmaceutical Sciences*, 14th Ed., J.E. Hoover et al., eds., Mack Publishing Co., Easton, Pennsylvania (1970).

Sawhney, A.S. et al., "Bioerodible Hydrogels Based on Photopolymerized Poly(ethylene glycol)–co–poly($\alpha$–hydroxy acid) Diacrylate Macromers," *Macromolecules*, 26:581–587 (1993).

Shah, K.R., "Novel Two–Phase Polymer System," *Polymer*, 28:1212–1216 (1987).

Shah, K.R., "Hydropholic–Hydrophobic Domain Polymer Systems," *Water Soluble Polymers*, Chap. 30, Shalaby, S.W. et al., eds., Amer. Chem. Soc., Washington, D.C., 467–483 (1991).

Shalaby, S.W., "Bioabsorbable Polymers", *Encyclopedia of Pharmaceutcal Technology*, Swarbrick, J. et al., eds., Marcel Dekker, Inc., New York, 1:465–476 (1988).

Shalaby, S.W. et al., "In Vitro and In Vivo Studies of Enzyme–Digestible Hydrogels for Oral Drug Delivery," *J. Controlled Release*, 19:131–144 (1992).

Silberberg, A., "Network Deformation in Flow," *Molecular Basis of Polymer Networks*, Baumgartner, A. et al., eds., Springer–Verlag, Berlin, 42:147–151 (1989).

Smith, K.L. et al., "Association Reactions for Poly(alkylene Oxides) and Polymeric Poly (carboxylic Acids)," *Ind. Eng. Chem.*, 51(11):1361–1364 (1959).

*The Drug, The Nurse, The Patient (Including Current Drug Handbook)*, Falconer's 7th Ed., W.B. Saunders Co., Philadelphia, Pennsylvania (1974).

* cited by examiner

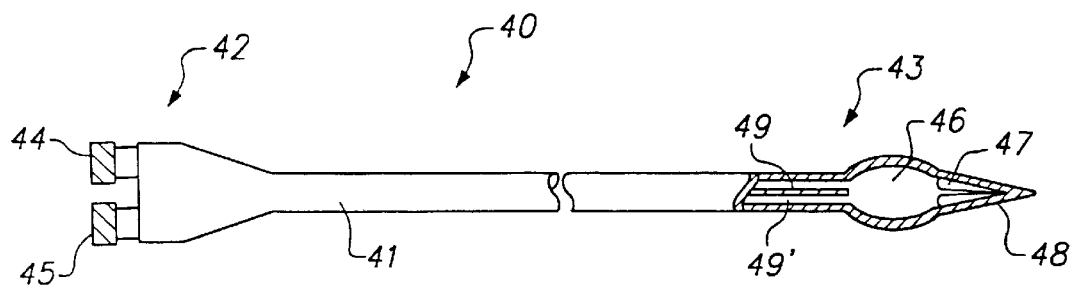
FIG. 3
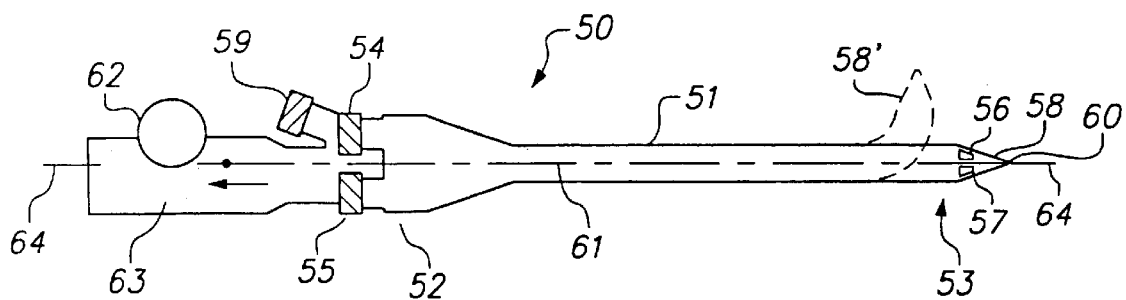
FIG. 4
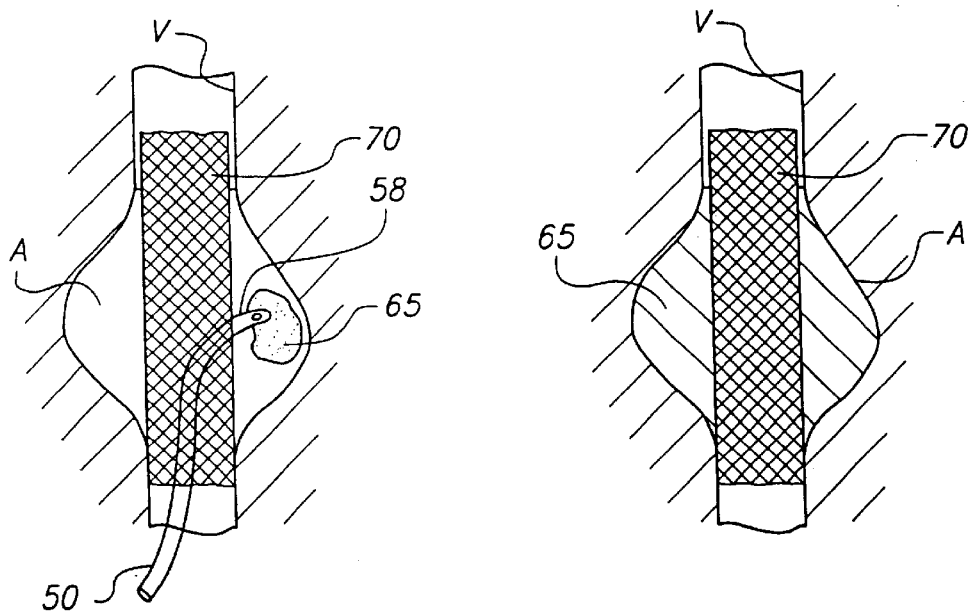
FIG. 5A        FIG. 5B

METHODS AND APPARATUS FOR INTRALUMINAL DEPOSITION OF HYDROGELS

REFERENCE TO RELATED APPLICATIONS

This application is a continuation-in-part of U.S. patent application Ser. No. 09/133,950, filed Aug. 14, 1998 now U.S. Pat. No. 6,152,943.

FIELD OF THE INVENTION

This present invention relates to methods and apparatus for applying hydrogels within body lumens to occlude, coat or support tissue. More particularly, the present invention relates apparatus and methods for intraluminally delivering two or more liquid components to form a hydrogel implant in situ.

BACKGROUND OF THE INVENTION

Hydrogels are materials that absorb solvents (such as water), undergo rapid swelling without discernible dissolution, and maintain three-dimensional networks capable of reversible deformation. See, e.g., Park, et al., *Biodegradable Hydrogels for Drug Delivery*, Technomic Pub. Co., Lancaster, Pa. (1993).

Hydrogels may be uncrosslinked or crosslinked. Uncrosslinked hydrogels are able to absorb water but do not dissolve due to the presence of hydrophobic and hydrophilic regions. A number of investigators have explored the concept of combining hydrophilic and hydrophobic polymeric components in block (Okano, et al., "Effect of hydrophilic and hydrophobic microdomains on mode of interaction between block polymer and blood platelets", *J. Biomed. Mat. Research*, 15:393–402 (1981), or graft copolymeric structures (Onishi, et al., in *Contemporary Topics in Polymer Science*, (Bailey & Tsuruta, Eds.), Plenum Pub. Co., New York, 1984, p. 149), and blends (Shah, "Novel two-phase polymer system," *Polymer*, 28:1212–1216 (1987) and U.S. Pat. No. 4,369,229 to Shah) to form the "hydrophobic-hydrophilic" domain systems, which are suited for thermoplastic processing. See, Shah, Chap. 30, in *Water Soluble Polymers* (Shalaby et al., Eds.), Vol. 467, ACS-Symp. Ser., Amer. Chem. Soc., Washington (1991). These uncrosslinked materials can form hydrogels when placed in an aqueous environment.

Covalently crosslinked networks of hydrophilic polymers, including water-soluble polymers are traditionally denoted as hydrogels (or aquagels) in the hydrated state. Hydrogels have been prepared based on crosslinked polymeric chains of methoxypoly(ethylene glycol) monomethacrylate having variable lengths of the polyoxyethylene side chains, and their interaction with blood components has been studied (Nagaoka et al., in *Polymers as Biomaterial* (Shalaby et al., Eds.) Plenum Press, 1983, p. 381). A number of aqueous hydrogels have been used in various biomedical applications, such as, for example, soft contact lenses, wound management, and drug delivery.

Non-degradable hydrogels made from poly(vinyl pyrrolidone) and methacrylate have been fashioned into fallopian tubal occluding devices that swell and occlude the lumen of the tube. See, Brundin, "Hydrogel tubal blocking device: P-Block", in *Female Transcervical Sterilization*, (Zatuchini et al., Eds.) Harper Row, Philadelphia (1982). Because such hydrogels undergo a relatively small amount of swelling and are not absorbable, so that the sterilization is not reversible, the devices described in the foregoing reference have found limited utility.

It therefore would be desirable to provide methods and apparatus of using hydrogel materials to temporarily occlude a body lumen that overcome the drawbacks of previously known compositions and methods.

Abnormal vascular connections, known as arteriovenous malformations (AVMs), may develop either as a congenital defect or as a result of iatrogenic or other trauma. An AVM may lead to a substantial diversion of blood from the intended tissue and may consequently engender a variety of symptoms, including those leading to morbidity. Subdural hematomas and bleeding also may occur as a result of the presence of an AVM.

Surgical intervention is often undertaken to correct AVMs. Interventional radiologic approaches also are used to obliterate AVMs by embolization, in which the goal of embolization is to selectively obliterate an abnormal vascular structure, while preserving blood supply to surrounding normal tissue. Embolization typically is accomplished using low-profile soft microcatheters that allow superselective catheterization into the brain to deliver an embolic material under fluoroscopic guidance. Various embolic materials have been used in endovascular treatment in the central nervous system, such as cyanoacrylates, ethylene-vinyl alcohol copolymer mixtures, ethanol, estrogen, poly(vinyl acetate), cellulose acetate polymer, poly (vinyl alcohol), gelatin sponges, microfibrillar collagen, surgical silk sutures, detachable balloons, and coils. Delivery of these embolic materials often requires the use of elaborate delivery systems.

It would therefore be desirable to provide methods and apparatus for using multi-component hydrogel systems as embolic materials to occlude arteriovenous malformations, thus taking advantage of the relative ease with which the crosslinkable components of a hydrogel system may be delivered.

U.S. Pat. No. 5,785,679 to Abolfathi et al. describes methods and apparatus for excluding aneurysms with in-situ moldable agents, such as water-swellable and thermally initiated hydrogels, by intraluminally or laparoscopically injecting the moldable material around an inflatable member disposed in the vessel. The reference also describes embedding a stent in the moldable material for enhanced support. International Publication No. WO 95/08289 describes a similar system for excluding aneurysms using photopolymerizable materials. Both systems employ inflatable members that partially or completely occlude the vessel and mold the moldable material during polymerization.

It would therefore be desirable to provide methods and apparatus for excluding aneurysms using hydrogels that are formed in situ, without partially or completely occluding the vessel.

SUMMARY OF THE INVENTION

In view of the foregoing, it is an object of the present invention to provide methods and apparatus of using hydrogel materials to temporarily occlude a body lumen that overcome the drawbacks of previously known compositions and methods.

It is another object of this invention to provide methods and apparatus for using multi-component hydrogel systems as embolic materials to occlude arteriovenous malformations, thus taking advantage of the relative ease with which the crosslinkable components of a hydrogel system may be delivered.

It is a further object of the present invention to provide methods and apparatus for excluding aneurysms using hydrogels that are formed in situ, without partially or completely occluding the vessel.

These and other objects of the invention are accomplished by providing apparatus and methods for delivering and applying crosslinkable compositions (referred to herein as "prepolymers") to selected tissue lumens, and then initiating a reaction in situ by allowing the prepolymers to either mix with other prepolymers and initiate a crosslinking process, or to be exposed to the physiological environment to initiate the crosslinking process. The crosslinkable solutions used with the apparatus may be crosslinked using either physical crosslinking, chemical crosslinking, or both.

In accordance with the present invention, delivery systems are provided for delivering separate prepolymer components of a hydrogel system, without premature crosslinking within the delivery system. In one embodiment, the delivery system includes an occlusive element for anchoring a distal end and isolating the region in which the hydrogel is to be formed in situ. In another embodiment, the delivery system may include variable stiffness regions to enable passage through tortuous anatomy. In yet another embodiment, the delivery system includes a steerable tip. In still further alternative embodiments, the prepolymer components of the hydrogel system may be mixed together in a mixing chamber disposed in a distal region of the delivery system, and then extruded into the body lumen or void during the crosslinking process, to reduce washout or dilution of the components.

Methods of using the inventive apparatus to apply a polymeric material to a lumen as a coating, or to fill in a luminal defect, such as an aneurysm, to occlude an abnormal vascular structure, such as an arteriovenous malformation or arteriovenous fistula whether natural or induced, and to occlude a natural lumen for a therapeutic purpose, within a human or animal patient, also are provided.

BRIEF DESCRIPTION OF THE DRAWINGS

Further features of the invention, its nature and various advantages will be more apparent from the accompanying drawings and the following detailed description of the preferred embodiments, in which:

FIG. 3 is a side view, partly in section, of a delivery system of the present invention having a flexible distal region and mixing chamber;

FIG. 4 is a side view of a delivery system of the present invention having a steerable tip; and FIGS. 5A and 5B illustrate a method of using the apparatus of FIG. 4 to exclude an aneurysm.

DETAILED DESCRIPTION OF THE INVENTION

Figure 1A:
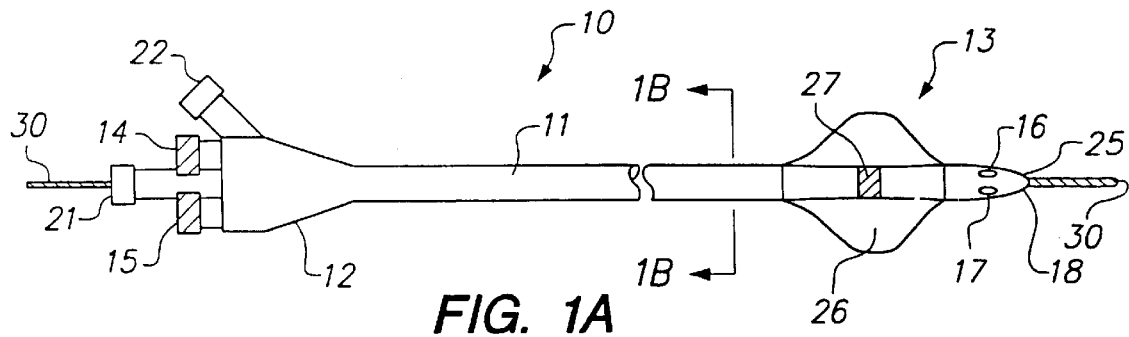
FIGS. 1A and 1B are, respectively, a side view and cross-sectional view, taken along view line 1B—1B, of a delivery system constructed in accordance with the present invention for injecting two in situ crosslinkable components to occlude a body lumen or arteriovenous malformation.

The present invention is directed to methods and apparatus for intraluminally delivering two or more crosslinkable solutions to form hydrogel implants in situ. The following written description describes multi-component hydrogel systems suitable for such use, delivery systems for depositing such hydrogel systems, and provides illustrative examples of use of the inventive apparatus and methods.

Hydrogel Systems Suitable For Use

Crosslinkable solutions preferred for use in accordance with the principles of the present invention include those that may be used to form implants in lumens or voids, and may form physical crosslinks, chemical crosslinks, or both. Physical crosslinks may result from complexation, hydrogen bonding, desolvation, Van der Waals interactions, ionic bonding, etc., and may be initiated by mixing two components that are physically separated until combined in situ, or as a consequence of a prevalent condition in the physiological environment, such as temperature, pH, ionic strength, etc. Chemical crosslinking may be accomplished by any of a number of mechanisms, including free radical polymerization, condensation polymerization, anionic or cationic polymerization, step growth polymerization, etc. Where two solutions are employed, each solution preferably contains one component of a co-initiating system and crosslink on contact. The solutions are separately stored and mix when delivered into a tissue lumen.

Hydrogels suitable for use in accordance with the principles of the present invention preferably crosslink spontaneously without requiring the use of a separate energy source. Such systems allow good control of the crosslinking process, because gelation does not occur until the catheter is actuated and mixing of the two solutions takes place. If desired, one or both crosslinkable solutions may contain contrast agents or other means for visualizing the hydrogel implant. Alternatively, a colored compound may be produced as a byproduct of the reactive process. The crosslinkable solutions also may contain a bioactive drug or therapeutic compound that is entrapped in the resulting implant, so that the hydrogel implant serves a drug delivery function.

Properties of the hydrogel system, other than crosslinkability, preferably should be selected according to the intended application. For example, if the hydrogel implant is to be used to temporarily occlude a reproductive organ, such as a fallopian tube, it is preferable that the hydrogel system undergo significant swelling and be biodegradable. Alternatively, the hydrogel may have thrombotic properties, or its components may react with blood or other body fluids to form a coagulum.

Other applications may require different characteristics of the hydrogel system. There is extensive literature describing the formulation of crosslinkable materials for particular medical applications, which formulae may be readily adapted for use herein with little experimentation. More generally, the materials should be selected on the basis of exhibited biocompatibility and lack of toxicity. Also, the hydrogel solutions should not contain harmful or toxic solvents.

Additionally, the hydrogel system solutions should not contain harmful or toxic solvents. Preferably, the solutions are substantially soluble in water to allow application in a physiologically-compatible solution, such as buffered isotonic saline. Water-soluble coatings may form thin films, but more preferably form three-dimensional gels of controlled thickness. It is also preferable in cases that the coating be biodegradable, so that it does not have to be retrieved from the body. Biodegradability, as used herein, refers to the predictable disintegration of the coating into molecules small enough to be metabolized or excreted under normal physiological conditions.

Polymers Suitable for Physical Crosslinking

Physical crosslinking may be intramolecular or intermolecular or in some cases, both. For example, hydrogels can be formed by the ionic interaction of divalent cationic metal ions (such as $Ca^{+2}$ and $Mg^{+2}$) with ionic polysaccharides such as alginates, xanthan gums, natural gum, agar, agarose, carrageenan, fucoidan, furcellaran, laminaran, hypnea, eucheuma, gum arabic, gum ghatti, gum karaya, gum tragacanth, locust beam gum, arabinogalactan, pectin, and amylopectin. These crosslinks may be easily reversed by exposure to species that chelate the crosslinking metal ions, for example, ethylene diamine tetraacetic acid. Multifunctional cationic polymers, such as poly(1-lysine), poly (allylamine), poly(ethyleneimine), poly(guanidine), poly (vinyl amine), which contain a plurality of amine functionalities along the backbone, may be used to further induce ionic crosslinks.

Hydrophobic interactions are often able to induce physical entanglement, especially in polymers, that induces increases in viscosity, precipitation, or gelation of polymeric solutions. For example, poly(oxyethylene)-poly (oxypropylene) block copolymers, available under the trade name of PLURONIC®, BASF Corporation, Mount Olive, N.J., are well known to exhibit a thermoreversible behavior in solution. Thus, an aqueous solution of 30% PLURONIC® F-127 is a relatively low viscosity liquid at 4° C. and forms a pasty gel at physiological temperatures due to hydrophobic interactions. Other block and graft copolymers of water soluble and insoluble polymers exhibit similar effects, for example, copolymers of poly(oxyethylene) with poly (styrene), poly(caprolactone), poly(butadiene) etc.

Techniques to tailor the transition temperature, i.e. the temperature at which an aqueous solution transitions to a gel due to physical linking, are per se known. For example, the transition temperature may be lowered by increasing the degree of polymerization of the hydrophobic grafted chain or block relative to the hydrophilic block. Increase in the overall polymeric molecular weight, while keeping the hydrophilic: lipophilic ratio unchanged also leads to a lower gel transition temperature, because the polymeric chains entangle more effectively. Gels likewise may be obtained at lower relative concentrations compared to polymers with lower molecular weights.

Solutions of other synthetic polymers such as poly(N-alkylacrylamides) also form hydrogels that exhibit thermoreversible behavior and exhibit weak physical crosslinks on warming. During deposition of thermoreversible solutions, the solutions may cooled so that, upon contact with tissue target at physiological temperatures, viscosity increases as a result of the formation of physical crosslinks. Similarly, pH responsive polymers that have a low viscosity at acidic or basic pH may be employed, and exhibit an increase in viscosity upon reaching neutral pH, for example, due to decreased solubility.

For example, polyanionic polymers such as poly(acrylic acid) or poly(methacrylic acid) possess a low viscosity at acidic pHs that increases as the polymers become more solvated at higher pHs. The solubility and gelation of such polymers further may be controlled by interaction with other water soluble polymers that complex with the polyanionic polymers. For example, it is well known that poly(ethylene oxides) of molecular weight over 2,000 dissolve to form clear solutions in water. When these solutions are mixed with similar clear solutions of poly(methacrylic acid) or poly(acrylic acid), however, thickening, gelation, or precipitation occurs depending on the particular pH and conditions used (for example see Smith et al., "Association reactions for poly(alkylene oxides) and poly(carboxylic acids)," Ind. Eng. Chem., 51:1361 (1959). Thus, a two component aqueous solution system may be selected so that the first component (among other components) consists of poly(acrylic acid) or poly(methacrylic acid) at an elevated pH of around 8–9 and the other component consists of (among other components) a solution of poly(ethylene glycol) at an acidic pH, such that the two solutions on being combined in situ result in an immediate increase in viscosity due to physical crosslinking.

Physical gelation also may be obtained in several naturally existing polymers too. For example gelatin, which is a hydrolyzed form of collagen, one of the most common physiologically occurring polymers, gels by forming physical crosslinks when cooled from an elevated temperature. Other natural polymers, such as glycosaminoglycans, e.g., hyaluronic acid, contain both anionic and cationic functional groups along each polymeric chain. This allows the formation of both intramolecular as well as intermolecular ionic crosslinks, and is responsible for the thixotropic (or shear thinning) nature of hyaluronic acid. The crosslinks are temporarily disrupted during shear, leading to low apparent viscosities and flow, and reform on the removal of shear, thereby causing the gel to reform.

Macromers Suitable for Chemical Crosslinking

Water soluble polymerizable polymeric monomers having a functionality >1 (i.e., that form crosslinked networks on polymerization) and that form hydrogels are referred to hereinafter as "macromers". Several functional groups may be used to facilitate chemical crosslinking reactions. When these functional groups are self condensible, such as ethylenically unsaturated functional groups, the crosslinker alone is sufficient to result in the formation of a hydrogel, when polymerization is initiated with appropriate agents. Where two solutions are employed, each solution preferably contains one component of a co-initiating system and crosslink on contact. The solutions are stored in separate compartments of a delivery system, and mix either when deposited on or within the tissue.

An example of an initiating system suitable for use in the present invention is the combination of a peroxygen compound in one solution, and a reactive ion, such as a transition metal, in another. Other means for crosslinking macromers to form tissue implants in situ also may be advantageously used, including macromers that contain groups that demonstrate activity towards functional groups such as amines, imines, thiols, carboxyls, isocyanates, urethanes, amides, thiocyanates, hydroxyls, etc., which may be naturally present in, on, or around tissue. Alternatively, such functional groups optionally may be provided in the lumen as part of the hydrogel system.

Preferred hydrogel systems are those biocompatible multi-component systems that spontaneously crosslink when the components are mixed, but wherein the two or more components are individually stable. Such systems include, for example, contain macromers that are di or multifunctional amines in one component and di or multifunctional oxirane containing moieties in the other component. Other initiator systems, such as components of redox type initiators, also may be used. The mixing of the two or more solutions may result in either an addition or condensation polymerization that further leads to the formation of an implant.

Monomers

Any monomer capable of being crosslinked to form a biocompatible implant may be used. The monomers may be small molecules, such as acrylic acid or vinyl caprolactam, larger molecules containing polymerizable groups, such as acrylate-capped polyethylene glycol (PEG-diacrylate), or other polymers containing ethylenically-unsaturated groups, such as those of U.S. Pat. No. 4,938,763 to Dunn et al, U.S. Pat. Nos. 5,100,992 and 4,826,945 to Cohn et al, U.S. Pat.

Nos. 4,741,872 and 5,160,745 to De Luca et al., or U.S. Pat. No. 5,410,016 to Hubbell et al.

Preferred monomers are the biodegradable, water-soluble macromers described in U.S. Pat. No. 5,410,016 to Hubbell et al., which is incorporated herein by reference. These monomers are characterized by having at least two polymerizable groups, separated by at least one degradable region. When polymerized in water, they form coherent gels that persist until eliminated by self-degradation. In the most preferred embodiment, the macromer is formed with a core of a polymer that is water soluble and biocompatible, such as the polyalkylene oxide polyethylene glycol, flanked by hydroxy acids such as lactic acid, having acrylate groups coupled thereto. Preferred monomers, in addition to being biodegradable, biocompatible, and non-toxic, also will be at least somewhat elastic after crosslinking or curing.

It has been determined that monomers with longer distances between crosslinks are generally softer, more compliant, and more elastic. Thus, in the polymers of Hubbell, et al., increased length of the water-soluble segment, such as polyethylene glycol, tends to enhance elasticity. Molecular weights in the range of 10,000 to 35,000 of polyethylene glycol are preferred for such applications, although ranges from 3,000 to 100,000 also are useful.

Initiating Systems

Metal ions may be used either as an oxidizer or a reductant in redox initiating systems. For example, ferrous ions may be used in combination with a peroxide or hydroperoxide to initiate polymerization, or as parts of a polymerization system. In this case, the ferrous ions serve as a reductant. In other previously known initiating systems, metal ions serve as an oxidant.

For example, the ceric ion (4+ valence state of cerium) interacts with various organic groups, including carboxylic acids and urethanes, to remove an electron to the metal ion, and leave an initiating radical behind on the organic group. In such a system, the metal ion acts as an oxidizer. Potentially suitable metal ions for either role are any of the transition metal ions, lanthanides and actinides, which have at least two readily accessible oxidation states.

Preferred metal ions have at least two states separated by only one difference in charge. Of these, the most commonly used are ferric/ferrous; cupric/cuprous; ceric/cerous; cobaltic/cobaltous; vanadate V vs. IV; permanganate; and manganic/manganous. Peroxygen containing compounds, such as peroxides and hydroperoxides, including hydrogen peroxide, t-butyl hydroperoxide, t-butyl peroxide, benzoyl peroxide, cumyl peroxide, etc. may be used.

Thermal initiating systems may be used rather than the redox-type systems described hereinabove. Several commercially available low temperature free radical initiators, such as V-044, available from Wako Chemicals USA, Inc., Richmond, Va., may be used to initiate free radical crosslinking reactions at body temperatures to form hydrogel implants with the aforementioned monomers.

Delivery Systems For Forming Hydrogel Implants In Situ

Figure 1B:
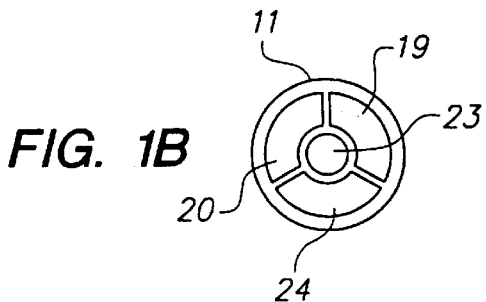

Referring to FIGS. 1A and 1B, an illustrative delivery system constructed in accordance with the principles of the present invention is described. Delivery system 10 comprises multi-lumen catheter 11 having proximal end 12 and distal end 13. Proximal end 12 includes inlet ports 14 and 15 coupled to respective outlet ports 16 and 17 disposed near tip 18 via separate lumens 19 and 20, respectively. Guidewire inlet port 21 and balloon inflation port 22 are coupled via separate lumens 23 and 24, respectively, to guidewire outlet port 25 and balloon 26.

Radio-opaque marker band 27 is disposed within balloon 26, or elsewhere on distal end 13, to assist in positioning distal end 13 of delivery system 10 within a body lumen under fluoroscopic guidance. Guidewire 30 extends through guide wire inlet port 21 and outlet port 25, and may be used, for example, to intraluminally guide tip 18 of delivery system 10 to a treatment site, such as a fallopian tube or a peripheral or coronary artery. Balloon 26 may be inflated to anchor catheter 11 in position within a body lumen during formation of a hydrogel implant, and may also occlude a lumen to prevent fluid flow from diluting the prepolymer solutions during gelation. Delivery system 10 optionally may include an outer sheath that surrounds balloon 26 when the balloon is deflated.

Alternatively, catheter 11 may be configured to have only three lumens, for example, lumens 19, 23 and 24 of the embodiment of FIG. 1B, thus omitting inlet port 15 and outlet port 17. In this case, lumen 19 couples inlet port 14 to outlet port 16, lumen 23 couples guidewire inlet port 21 to outlet port 25, and lumen 24 couples inflation port 22 to the interior of balloon 26. In operation, lumen 23 initially may be used to position the delivery catheter 10 in a desired position, and guidewire 30 is then withdrawn. A first crosslinkable solution is then injected through lumen 23 while a second rosslinkable solution is injected through lumen 19. The crosslinkable solutions crosslink when mixed to form a hydrogel implant.

As a further alternative to the embodiment of FIGS. 1, guidewire lumen 23 need not extend the length of the catheter to form a so-called "over the wire" catheter. Instead, guidewire lumen 23 may be configured as a shorter lumen that exits catheter 11 through a skive just proximal of balloon 26 to form a so-called "rapid exchange" catheter, as described, for example, in U.S. Pat. No. 4,762,129 to Bonzel.

Delivery system 10 may be fabricated of any of a wide variety of materials that are sufficiently flexible and biocompatible. For example, polyethylenes, nylons, polyvinylchlorides, polyether block amides, polyurethanes, and other similar materials are suitable. It is preferred that the material have a low coefficient of friction, at least within the lumen 23, to facilitate movement of the delivery system over guidewire 30. Alternatively, the lumen 23 may be coated with a lubricious material to lower frictional resistance between the wall of lumen 23 and guidewire 30. For example, if catheter 11 comprises a urethane, a polyethylene oxide-based material may be coated onto the lumens of the device to provide lubricity.

Balloon 26 preferably comprises a relatively compliant material to enable delivery system 10 to provide complete occlusion of a body lumen over a range of lumen diameters. In addition, compliant balloons are less likely to cause trauma to the tissue lumen, thereby reducing the potential for complications as a result of overinflation. Suitable compliant balloon materials include, but are not limited to, latex, urethanes, and polyether block amides.

Delivery system 10 should be of a size appropriate to facilitate delivery, to have a minimum profile, and cause minimal trauma when inserted and advanced to a treatment site. In an embodiment suitable for forming hydrogel implants in fallopian tubes, peripheral or coronary vessels, delivery system 10 preferably is no larger than about 1.6 mm (0.065 inches) to allow delivery through a standard coronary guide catheter. The device preferably also is sized to easily pass through obstructed lesions and to be deliverable over small diameter guidewires, such as guidewires having a diameter of approximately 0.30–0.45 mm (0.012–0.018 inches), as commonly used in the coronary arteries.

A molding balloon, such as described in the abovementioned U.S. Pat. No. 5,785,679 or International Publication No. WO 95/08289 optionally may be substituted for balloon 26 where it is desired to isolate a space in which a hydrogel implant is to be formed. Such molding balloons preferably comprise polyethylene terephthalates or crosslinked polyethylenes, which exhibit little change in diameter over a wide range of inflation pressures. Irradiated polyethylenes have low surface energy and therefore are also desirable to minimize the effect of the polymeric materials sticking to the molding balloon. Alternatively, a coating having low surface energy may be used to facilitate release of the polymeric material from other balloons. Such coatings include silicone oils, fluoropolymers, surfactants, hydrogels or other hydrophobic materials having low surface energy.

Since non-compliant balloons, when inflated, maintain a substantially constant size regardless of internal pressure, it is preferred that in the case of gel coating applications, such as described in U.S. Pat. No. 5,328,471 to Slepian, the balloon be sized approximately 0.20–1.0 mm less than the diameter of the vessel to be treated. In this manner a gel coating having a thickness of approximately 0.10–0.50 mm may be disposed on an interior of a lumen. Alternatively, a moderately compliant balloon, e.g., made of a urethane, a polyolefin or a nylon, may be used to treat a wider range of vessel diameters while allowing a tailored gel thickness.

Figure 2:
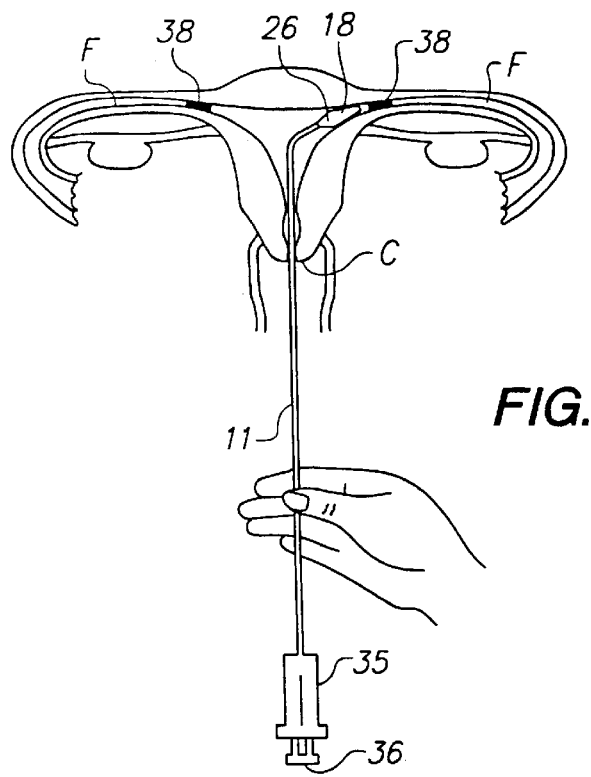
FIG. 2 illustrates a method of using the apparatus of FIG. 1 to occlude fallopian tubes.

Referring now to FIG. 2, a method of using delivery system 10 of FIG. 1 is described for delivering hydrogel-forming precursor materials within a fallopian tube lumen. Fallopian tubes F are accessed by passing catheter 11 through cervix C under fluoroscopic guidance. Proximal end 12 of delivery system 10 is coupled to dual syringe-type device 35 having actuator 36 that allows simultaneous injection of two crosslinkable solutions, described hereinabove. Balloon 26 may be inflated with a fluid containing a contrast agent to verify placement of tip 18.

If desired, following inflation of balloon 26, the treatment space may be filled or flushed with a solution, such as an inert saline solution, to remove blood and other biological fluids from the treatment space. Delivery system 10 optionally may include an additional lumen to permit such flushing liquids to exit the treatment space. Alternatively, a non-inert solution, such as a solution containing a pharmaceutical agent, may be injected into the treatment space.

Actuator 36 is then depressed so that the solutions are delivered through outlet ports 16 and 17 within the fallopian tube distal of balloon 26. The solutions are allowed to mix and crosslink, thus forming lug 38 that occludes the fallopian tube. Balloon 26 is then deflated and catheter 11 withdrawn.

Referring now to FIG. 3, an alternative embodiment of a delivery system constructed in accordance with the principles of the present invention is described. Delivery system 40 comprises dual-lumen catheter 41 having proximal region 42 and flexible distal region 43. Proximal region 42 includes inlet ports 44 and 45 coupled to optional mixing chamber 46 and outlet ports 47 disposed on tip 48. One or more radio-opaque marker bands (not shown) may be disposed in distal region 43 to assist in positioning delivery system 40 within a natural or induced body lumen under fluoroscopic guidance. Delivery system 40 may have a very small profile for very small vessels, e.g., below 1.6 mm, for use in cerebrovascular vessels.

Delivery system 40 is particularly suitable for use where the polymeric material is to be applied to a surface of a natural or induced body lumen or void, and through which a body fluid is not flowing at very high velocity. Prepolymer solutions are injected via lumens 49 and 49' into mixing chamber at a rate selected so that the prepolymer solutions begin crosslinking in chamber 46, with the resulting partially-formed gel being extruded through outlet ports 47 into the lumen or void. In this manner, wash-out or dilution of the prepolymer solutions during deposition is reduced or eliminated, thereby reducing the risk that the prepolymer solutions will cause embolization in other portions of, for example, the vascular system.

Delivery system 40 therefore prevents premature crosslinking of the prepolymer solutions, while also enabling the solutions to be mixed and partially gelled before being deposited in the body lumen or void. Delivery system may be especially useful in depositing hydrogel systems that form both physical and chemical crosslinks, wherein the physical crosslinking is accomplished by mixing the prepolymer solutions in mixing chamber 46. The partial gel extruded from mixing chamber 46 through outlet ports 47 then may have sufficient mechanical integrity to remain in position in the body lumen or void during the chemical crosslinking process.

Alternatively, distal region 43 of delivery system 40 may comprise a very flexible material, may omit mixing chamber 46, and may have a smaller diameter than that of catheter 41. Distal region 43 may be induction welded, bonded or glued to the distal end of catheter 41 by any one of several ways per se known. Because distal region 43 is made from a very flexible material, distal tip 48 may be "flow directed" (i.e., tip 48 will tend to follow the direction of fluid flow within the lumen).

In treating cerebrovascular abnormalities, such as arteriovenous malformations or tumors, it is desirable that the vasculature be embolized only within the abnormal part of the network. This may be accomplished by radiographically monitoring placement of tip 48, and when proper placement is ascertained, slowly injecting the prepolymer solutions. Upon mixing within the lumen of the vessels, crosslinking occurs and a hydrogel is formed that occludes the abnormal vasculature. The prepolymer solutions also may contain dissolved radiocontrast agent to assist in visualizing placement of the hydrogel.

With respect to FIG. 4, a further alternative embodiment of a delivery system constructed in accordance with the principles of the present invention is described. Delivery system 50 comprises multi-lumen catheter 51 having proximal end 52 and distal end 53. Proximal end 52 includes inlet ports 54 and 55 coupled to respective outlet ports 56 and 57 disposed on tip 58. Guidewire inlet port 59 is coupled to guidewire outlet port 60. Delivery system 50 may include a balloon (not shown) and one or more radio-opaque marker bands (not shown) on distal end 53 to assist in positioning and anchoring delivery system 50 within a body lumen.

In accordance with one aspect of the present invention, tip 58 is connected via tensioning cable 61 to axle 62 located on handle 63. Tensioning cable 61 slidingly extends through a lumen in catheter 51 that is eccentric with central axis 64 of catheter 51. Thus, when tensioning cable 61 is put in tension, for example, by a predetermined amount of rotation of axle 62, tip 58 deflects away from central axis 64 a predetermined amount (as shown by dotted line 58' in FIG. 4). Delivery system 50 is particularly well-suited for use in conjunction with other commonly used intraluminal devices, such as stents, stent grafts, etc., to manage intraluminal anomalies.

Referring now to FIGS. 5A and 5B, a method of using delivery system 50 for treating aneurysms is described that overcomes some of the drawbacks of previously known methods, especially as relates to use of inflatable members to as molding elements.

In FIG. 5A, wire mesh stent 70, such as described in U.S. Pat. No. 4,655,771 to Wallsten, is disposed in vessel V to span saccular aneurysm A and define an intraluminal space between the exterior of the stent and the interior wall of the aneurysm. Delivery system 50 is then advanced into the interior of stent 70, and tip 58 is deflected using tensioning cable 61, as described hereinabove, to deflect tip 58 toward the interior surface of stent 70. Delivery system 50 is then advanced so that tip 58 passes through the wire mesh of stent 70 and is disposed within the aneurysm. If a balloon is provided on distal end 53 of delivery system 50, it is preferably inserted through the wire mesh of stent 70 and inflated to anchor tip 58 within the aneurysm.

Once proper placement of tip 58 of the delivery system is ascertained under radiographic guidance, the prepolymer solutions are injected into the intraluminal space defined by the exterior of stent 70 and the interior wall of aneurysm A. The prepolymer solutions preferably are selected so that they crosslink to form hydrogel 65 when mixed together. The prepolymer solutions also may have a radiographic presence to assist in visualizing gradual filling of the aneurysm. The resulting hydrogel 65 preferably is sufficiently malleable that it fills the intraluminal space defined by stent 70 without protruding through the wire mesh of stent 70.

Upon embolization, instillation of the prepolymer solutions is stopped and delivery system 50 is withdrawn. Any residual incomplete embolization is expected to be filled in by blood clot deposition within the defined space. The hydrogel also may be selected so as to promote thrombus formation, e.g., due to a physical structure or texture or entrapped bioactive compound. The prepolymer solutions also may contain dissolved or dispersed therapeutic compounds that are delivered intraluminally, in either a local or systemic fashion, by entrapment within the hydrogel.

Delivery system 50 therefore advantageously permits aneurysm A to be excluded from the flow path through vessel V, without using an inflatable member or significantly occluding flow through the vessel, as in previously known methods. Delivery system 50 and the foregoing method also may be advantageously used in many applications, so long as the stent or stent-graft defining the intraluminal space guides the appropriate deposition of the embolic material. Thus, for example, stent 70 may comprise any of a number of permeable members such as meshes, nets, stents struts, textile knitted, woven, or felted grafts, etc.

EXAMPLES

Example 1
Preparation of a Metered Liquid Embolic

Previously known treatments for embolization all basically rely on blood flow in one form or another to either react to the material or to carry it downstream to a geometric constraint, such as a tapered portion of a vessel. A drawback of this approach, however, is that it is difficult to form a short site-specific occlusive plug.

Numerous instances where it is desirable to form a discrete "plug" to block a specific region of a vessel or a specific side-branch, for example, to treat an arterio-venous fistula (AVF) or patent ductus arteriosus (PDA). A desirable configuration would have the ability to deploy a plug in a controlled manner even in the presence of blood flow to cause embolization of the vascular defect, but low risk of accidental embolization of other downstream structures. Physically, such materials could be delivered via a screw-driven syringe handle that allows the two materials not only to be delivered equally, but also to polymerize in a slow controlled manner to allow for specific amounts to be delivered at specific rates.

Several such mechanisms are available to control the process. In one embodiment, a two component redox polymerizable system (using free radical polymerizable macromers) that has limited miscibility in a warm aqueous environment may be used. Block copolymers of poly (ethylene glycol) (PEG) and poly (propylene glycol) (PPG), such as PLURONICS® (BASF Corp., Wyondette, N.J.) may be acrylated at the end groups to form F127 diacrylate macromers. These macromers, when used in aqueous solution in excess of approximately 15% concentration, tend to undergo thermal gelation at 37° C. due to a lower critical solution temperature transition. These materials, even though they are aqueous solutions, do not tend to dissolve in blood at physiological temperatures within a few seconds. This period of time is expected to be adequate for solutions of F127 diacrylate macromers to flow and conform to the vascular defect. The presence of the other solutions, which can be co- or subsequently infused, causes covalent cross-linking of the physically gelled macromers.

For example, one material configuration would be a solution A of 20% F127 diacrylate in water with 3000 ppm hydrogen peroxide and a solution B of 10% ferrous gluconate in water with a 30% metrizamide concentration in solution A as a radiopacifying agent. The materials are delivered through a co-axial catheter such as depicted in FIG. 1.

Alternatively, the materials could be mixed within the catheter and form the hydrogel within the catheter, and then extruded, as described for the embodiment of FIG. 3. This configuration allows the user to "extrude" the hydrogel from the catheter and form spaghetti-like strands that flow within the vessel and are interrupted by the discontinuation of infusion of one or both of the hydrogel materials. As a further alternative, the catheter may employ a coaxial design, with an outer extrusion projecting distal to a central extrusion.

An open system flow model was prepared using water at 37° C. at a flow rate of 80 cc/min and a pressure of 2.5 psi flowing into a bifurcated model with a hemostatic valve port for access. A 3.2 F co-axial catheter was introduced into the system through the hemostatic valve and advanced into one branch of the bifurcation model. Approximately 0.2 cc of solutions A and B (as described before) were infused simultaneously using a dual-syringe holder to allow equal infusion of both materials simultaneously at a rate of approximately 10 cc/min. The solutions immediately gelled and adhered to the tubing wall, subsequently building and forming a stiff gel "plug". A blue dye was introduced into the flow path and showed effective blockage of flow past the "plug". The pressure on the plug was increased to over 20 psi and did not allow flow of dye past it.

The above-described materials and apparatus also were used in a rabbit renal artery occlusion model in vivo. The materials were delivered to the left renal artery of the rabbit, under fluoroscopic guidance and two consecutive plugs were formed. These plugs were shown to occlude flow not only into the kidney but also occluded flow between the plugs that were spaced apart to show that flow was indeed interrupted. The plugs were visible under fluoroscopic visualization.

Example 2
Preparation of a Diffusely Polymerizing Liquid Embolic

Occasionally a need arises for a more diffuse, deeper-reaching liquid embolic that is capable of flowing for some distance within the vasculature. The system described in this example 2 allows deep introduction of liquid embolic materials before curing and may be especially useful in treating hypervascular tumors (among other such diffuse vascular diseases, including arterio venous malformations), where it is necessary to infuse the materials as deep as possible into the tumor vasculature, thereby embolizing all of collateral and side-branches of the effected vasculature.

In this example 2, a combination of slower polymerization and lower material viscosities is provided, consisting of two PEG di-acrylate (20% 3.35 da) solutions in water with 3000 ppm hydrogen peroxide and 2% Ferrous gluconate as solutions A and B, respectively, with a 30% metrizamide concentration in each solution as a radiopacifying agent. The time for gelation of the solutions after mixing is slightly greater than 1 second.

The solutions were introduced through a co-axial catheter with solution A introduced through one catheter lumen and solution B introduced through another lumen. The materials had relatively low viscosities and mixed distal to the catheter to polymerize downstream of the catheter, until adherence of the resulting gel occurred, thereby forming a long diffuse plug throughout the vasculature.

The materials described hereinabove also were used in an in vitro experiment using a coaxial delivery system, wherein at the catheter tip a central extrusion projected distal to an outer extrusion, thus allowing mixing to occur downstream from the distal tip of the catheter. In order to get slightly faster polymerization, a coaxial catheter may be used having a tip configuration where the inner lumen is recessed within the outer lumen or vice versa. In addition, surface coatings having a hydrophilic or hydrophobic nature may be used on the tip of the catheter to prevent "fouling" of the catheter tip and may promote clean detachment of the embolic material from the catheter. Such coatings and techniques are well known by those familiar with such art.

Example 3
Preparation of a Bio-Resorbable Liquid Embolic

In many instances, such as arterio-venous malformations ("AVM") or aneurysm, permanent occlusion of the defect is required. However, in other situations, permanent embolization may not be desirable. This may occur, for example, if one needs to re-visit a partially occluded tumor bed for further therapy. Previously known treatment modalities for hyper-vascular tumor embolization, with such materials as cyanoacrylate materials and small particle PVA, form a permanent "implant" that is either a hard polymeric branched implant or a plurality of small particles inhibiting flow by hitting a geometric restraint such as a tapered vessel diameter.

Because it may be necessary, however, to re-access the vessels of the tumor after they have been embolized, in case small collaterals have formed or side-branches had not been adequately embolized. With the previously known treatment modalities, it would be virtually impossible to re-canalize the tumor vasculature to continue treatment and successfully de-vascularize the tumor.

In accordance with the principles of the present invention, however, a liquid embolic material may be prepared having a persistence that is controlled to complete resorption after a predetermined period of time (1–3 weeks). The period of persistence is selected to be just long enough to effectively "starve" the tumor of its blood supply, while not being so long as to allow vessel stenosis from surrounding tissue necrosis. The disease site then may be re-accessed at a later time to evaluate and potentially repeat the liquid embolic treatment. Thus, a vessel may be re-embolized in enable embolization of previously untreated vessels. This procedure may be repeated a number of times, until the clinician is satisfied that the tumor has decreased to a resectable size.

A sample material configuration for use in the foregoing method comprises a solution A of 60% succinimidyl hydroxybutarate carboxy methyl terminated polyethylene glycol and 40% succinimidyl hydroxybutarate proprionate terminated polyethylene glycol (Shearwater Polymers, Huntsville, Ala.) in 90% pH 4 phosphate buffered saline and a solution B of 10% 8-arm 20K polyethylene glycol amine (Shearwater Polymers, Huntsville, Ala.) in pH 9.5 borate buffered saline.

Using a distal balloon catheter such as depicted in FIG. 1, these materials were delivered via the annular space and a resorbable "plug" was successfully formed in tubing that effectively withheld physiological pressure and flow. The plug, if left in place in an environment of physiologically buffered salt solutions, is expected to dissolve over a 10–14 day period into water soluble substances.

Example 4
Reversal of Occlusion

The embolic occlusion of lumens described in the foregoing example 3 may be reversed in ways other than using an absorbable material for the embolization process. For example, previously known embolectomy catheters and artherectomy devices also be used to remove the hydrogel embolus from within the lumen to reestablish flow through the lumen. Such reversible occlusion may also be important for achieving reversible sterilization in both male and female animals and humans. Previously known artherectomy devices, such as roto-blaters, also may advantageously be used to re-cannulate the lumens and reverse sterility in such cases.

Example 5
Preparation of a Vascular Puncture Closure Material

The foregoing materials also may be used in combination with a vascular puncture closure system to provide hemostasis after endovascular procedures. Previously known modalities include using fibrin and collagen based materials for hemostasis post-procedurally. For example, the Duett™ system developed Vascular Solutions, Inc., Minneapolis, Minn., comprises a device including a balloon catheter that is introduced through an introducer sheath into the vessel. The distal balloon is inflated and held against the vessel wall to control hemostasis. Once flow is stopped, fibrin materials are injected through the catheter in to the annular space between the delivery system and the introducer sheath. Problems arising from such systems, however, due to potential biocompatability of the fibrin materials, unpredictable cure rates, and potential introduction of the fibrin material into the vascular system.

By contrast, the methods and apparatus described herein provide immediate hemostasis using a bioabsorbable gel implant. In one embodiment, a low-profile delivery system is provided that utilizes a piston/cylinder assembly at the proximal end and a coated expandable mesh at the distal end. The device is introduced into an introducer sheath and deployed similar to an umbrella that would be propped against the interior of the vessel wall. The gel-forming materials then are introduced into the patient and into the annular space between the umbrella device and the introducer sheath.

As for the embodiment of FIG. 5, the materials mix in the annular space and cure in place using the umbrella device as a mold, thus preventing introduction of the embolic material into the vessel. A preferred material configuration for use in this example 5 comprises a solution A of 60% succinimidyl hydroxybutarate carboxy methyl terminated polyethylene glycol and 40% succinimidyl hydroxybutarate proprionate terminated poly ethylene glycol (Shearwater Polymers, Huntsville, Ala.) in 90% pH 4 phosphate buffered saline and a solution B of 10% 8-arm 20K poly ethylene glycol amine (Shearwater Polymers, Huntsville, Ala.) in pH 9.5 borate buffered saline.

Using a 6 mm tubing as a vascular model, an experiment was performed using preparations of the foregoing materials. The delivery device was a co-axial distal balloon catheter placed inside a 6F introducer sheath. The annular space of the catheter was used as a mixing chamber of the two materials, with distal flow occluded by inflation of the balloon. The materials were injected through the co-axial catheter and formed a plug in the tubing model. The balloon was deflated and the catheter was removed leaving the "plug" behind. The track left behind immediately closed and withheld physiological pressure and flow.

An experiment was performed in an in vivo porcine femoral artery. The animal's femoral artery was accessed percutaneously and 7F introducer set was placed. A wire-reinforced balloon catheter was advanced into the femoral artery past the distal tip of the introducer sheath. The balloon was slightly inflated and drawn back to the puncture site. The introducer sheath was removed as the balloon was pulled to come in contact with the inner wall of the femoral artery, effectively stopping blood flow from flowing into the track.

The two materials described hereinabove then were infused into the side port of the introducer sheath and allowed to mix within the sheath and polymerize. The materials also were infused as the introducer was removed while leaving the balloon in place to protect against downstream embolus. The materials filled the track, spilled out from the cavity, and polymerized, thus confirming polymerization. The balloon was then deflated and removed while holding pressure on the track site. Pressure was released and was shown to hold during leg movement. After dissection the gel plug was shown to be intact and effectively stop bleeding from the access site.

Example 6
A Kit For Operating Room Use

A kit for use in an operating room setting was assembled. The kit consists of two vial (West Co., Lionville, Pa.) with rubber stoppers and crimp caps that contain component A and component B respectively. Component A and component B may be present as pre-mixed solutions that are stable in liquid form. In this case the solutions may be sterile filtered as aqueous solutions, and then may be filled into vials or syringes. The vials or syringes may be aseptically packaged within a secondary pouch or vacuum formed contained. If this package is not done aseptically, then the kit may be packaged under clean conditions and sterilized by using a radiation process to sterilize the outside of the vials.

The kit also may consist of two powder filled vials containing component A and component B and two pre-filled syringes containing aqueous buffered solutions appropriate for reconstitution of the powders. The reconstitution fluids optionally may contain a radiopacifier either dispersed or dissolved within the solution to aid in the visualization of the deposition of the embolic agent. The syringes containing the reconstitution fluids may be used to reconstitute the respective powder containing vials at the time of the interventional procedure. Preferably, the buffers are selected in such a way so as to achieve a maximum "pot life" (or useful life after constitution of the powders) of the powders and yet allow for rapid reaction upon mixing of the two fluids at the site of deployment.

Alternatively, the reconstitution fluids also may be filled in vials that are drawn up into syringes within the operating room setting. All the components of the kits, the two vials containing component A and component B are placed in a vacuum formed insert (or other container or similar type well known to those familiar with the art of medical packaging), and sealed. This insert or pouch further may be placed in a secondary container to provide added protection of the kit from mechanical damage. The kit can then be terminally sterilized. In the event that free radically polymerizable materials are used, ethylene oxide sterilization of the powders is appropriate.

Example 7
Aneurysm Encasement of Stabilization

It is well known in the medical literature that cerebrovascular and other aneurysms may be stabilized internally and externally by either filling the aneurysm with, or encasing it in, plastic polymerizable materials, such as cyanoacrylates and PMMA cements. Such materials, however, have several disadvantages. For example, for external encasement of the aneurysm, such previously known materials have a low viscosity and do not form a coating easily. Cyanoacrylates, for example, form in brittle casings that fracture and may permit the aneurysm rupture. Such previously known materials also present toxicity problems.

It would be desirable to provide materials to encase aneurysms that are flexible, strong, rapidly polymerized, and are capable of being integrated with surrounding brain parenchymal tissues. In accordance with the principles of the present invention, PEG-diacrylate type materials of an appropriate molecular weight and concentration (such as the redox based foaming gels of Example 1) may be used to encase an aneurysm. The material may result in either a discrete gel or a foamed gel formation. The foamed gel may encourage incorporation of the gel within the tissue due to its porous structure, thus providing permanent stabilization of the aneurysm. The material also may be gradually applied using a dual syringe and a catheter based system such as described hereinabove to form an atraumatic coating.

In addition, a biocompatible fabric, such as are typically used to form synthetic grafts, may be used as a sheet and wrapped on the outside of an aneurysm. To address the potential that some gaps may remain around the fabric, which could cause aneurysmal weakening, a polymerizable hydrogel material is injected around and in between these spaces, thereby reinforcing the aneurysm. High pressures within the vessel would be held by the graft material, while the hydrogel provides a sealing action.

For aneurysms to be stabilized from within the vessel, most embolic materials present the inherent danger of embolizing downstream and causing infarcts and strokes. This danger may be minimized by the use of appropriate catheters, but the problem still is difficult to eliminate and has a very high risk of mortality associated with it. If a stent graft type of fabric graft material is deployed around the aneurysm and then the embolic material (such as the PEG-DA gels) are deployed using a catheter through the fabric material, it would be possible to use the graft material as a safety net to prevent any downstream embolization, and would result in a good filling of the aneurysm too.

While preferred illustrative embodiments of the invention are described above, it will be apparent to one skilled in the art that various changes and modifications may be made therein without departing from the invention and it is intended in the appended claims to cover all such changes and modifications which fall within the true spirit and scope of the invention.

What is claimed is:

1. Apparatus for depositing a polymer within a space within a body comprising:

a catheter having proximal and distal ends, first and second inlet ports disposed at the proximal end, first and second outlet ports disposed at the distal end adjacent to a balloon adapted to anchor within the space, a first lumen coupling the first inlet port to the first outlet port, and a second lumen coupling the second inlet port to the second outlet port, wherein the catheter is configured to inject into the space first and second fluent solutions that crosslink when mixed, the first and second solutions injected through the first and second lumens, respectively, the first and second lumens configured so that premature crosslinking of the solutions does not occur within the catheter.

2. The apparatus as defined in claim 1 wherein the catheter is configured to be transcervically inserted into a fallopian tube.

3. The apparatus as defined in claim 1 wherein the catheter further comprises a guidewire inlet port disposed at the proximal end, a guidewire outlet port disposed at the distal end, and a lumen coupling the guidewire inlet port to the guidewire outlet port.

4. The apparatus as defined in claim 1 wherein one of the first and second lumens is adapted to accept a guidewire to assist in placing the distal end within the space.

5. The apparatus as defined in claim 1 wherein a distal region of the catheter comprises a flexible material that permits the distal end of the catheter to be flow directed.

6. The apparatus of claim 1 further comprising at least one radio-opaque marker.

7. Apparatus for depositing a polymer within a space within a body comprising:

a catheter having proximal and distal ends, first and second inlet ports disposed at the proximal end, first and second outlet ports disposed at the distal end adjacent to an inflatable molding member, the first and second outlet ports exiting through a lateral surface of the catheter, a first lumen coupling the first inlet port to the first outlet port, and a second lumen coupling the second inlet port to the second outlet port, wherein the catheter is configured to inject into the space first and second fluent solutions that crosslink when mixed, the first and second solutions injected through the first and second lumens, respectively, the first and second lumens configured so that premature crosslinking of the solutions does not occur within the catheter.

8. The apparatus as defined in claim 7 further comprising a balloon adapted to anchor the distal end within the space.

9. The apparatus as defined in claim 7 wherein the catheter is configured to be transcervically inserted into a fallopian tube.

10. The apparatus as defined in claim 7 wherein the catheter further comprises a guidewire inlet port disposed at the proximal end, a guidewire outlet port disposed at the distal end, and a lumen coupling the guidewire inlet port to the guidewire outlet port.

11. The apparatus as defined in claim 7 wherein one of the first and second lumens is adapted to accept a guidewire to assist in placing the distal end within the space.

12. The apparatus as defined in claim 7 wherein a distal region of the catheter comprises a flexible material that permits the distal end of the catheter to be flow directed.

13. The apparatus of claim 7 further comprising at least one radio-opaque marker.

* * * * *

UNITED STATES PATENT AND TRADEMARK OFFICE
CERTIFICATE OF CORRECTION

PATENT NO. : 6,379,373 B1  Page 1 of 1
DATED : April 30, 2002
INVENTOR(S) : Amarpreet S. Sawhney and John Spiridigliozzi It is certified that error appears in the above-identified patent and that said Letters Patent is hereby corrected as shown below:

<u>Title page,</u>
Item [73], change Assignee from "Confluent Surgical, Inc." to -- Incept, LLC San Mateo, CA --

<u>Column 5,</u>
Line 43, please insert -- be -- following the word "may".

<u>Column 6,</u>
Line 51, please delete "contain" following the word "example,".

<u>Column 8,</u>
Line 24, please change "rosslinkable" to -- crosslinkable --.

<u>Column 10,</u>
Line 67, please delete "to" before the word "as".

<u>Column 14,</u>
Line 37, please insert -- by -- following the word "developed".
Line 42, please change "in to" to -- into --.
Line 44, please change "arising" to -- arise --.

<u>Column 15,</u>
Line 48, please change "contained" to -- container --.

Signed and Sealed this

Eighteenth Day of March, 2003

JAMES E. ROGAN
*Director of the United States Patent and Trademark Office*